United States Patent
Baker

(10) Patent No.: US 9,421,006 B2
(45) Date of Patent: Aug. 23, 2016

(54) CONNECTED FASTENERS, DELIVERY DEVICE AND METHOD

(75) Inventor: Steve G. Baker, Redmond, WA (US)

(73) Assignee: EndoGastric Solutions, Inc., Redmond, WA (US)

(*) Notice: Subject to any disclaimer, the term of this patent is extended or adjusted under 35 U.S.C. 154(b) by 1682 days.

(21) Appl. No.: 12/008,251

(22) Filed: Jan. 8, 2008

(65) Prior Publication Data

US 2008/0183195 A1    Jul. 31, 2008

Related U.S. Application Data

(60) Provisional application No. 60/879,402, filed on Jan. 8, 2007.

(51) Int. Cl.
*A61B 17/04* (2006.01)
*A61B 17/00* (2006.01)
*A61B 17/11* (2006.01)

(52) U.S. Cl.
CPC ....... *A61B 17/0401* (2013.01); *A61B 17/00234* (2013.01); *A61B 17/0487* (2013.01); *A61B 17/1114* (2013.01); *A61B 2017/0409* (2013.01); *A61B 2017/0417* (2013.01); *A61B 2017/0464* (2013.01); *A61B 2017/1142* (2013.01)

(58) Field of Classification Search
CPC ... A61F 5/0063; A61F 5/0033; A61F 5/0086; A61F 5/0083; A61F 5/0003; A61B 2017/0462
USPC .................. 606/144, 151, 153, 213, 215, 216
See application file for complete search history.

(56) References Cited

U.S. PATENT DOCUMENTS

| | | |
|---|---|---|
| 2,753,870 A | 7/1956 | Muffly |
| 3,875,928 A | 4/1975 | Angelchik |
| 4,006,747 A | 2/1977 | Kronenthal |
| 4,271,828 A | 6/1981 | Angelchik |
| 4,576,772 A | 3/1986 | Carpenter et al. |
| 4,595,007 A | 6/1986 | Mericle |
| 4,669,473 A | 6/1987 | Richards et al. |
| 4,696,300 A | 9/1987 | Anderson |
| 4,846,836 A | 7/1989 | Reich |
| 4,895,148 A | 1/1990 | Bays et al. |
| 4,921,479 A | 5/1990 | Grayzel |
| 5,006,106 A | 4/1991 | Angelchik et al. |

(Continued)

FOREIGN PATENT DOCUMENTS

| | | |
|---|---|---|
| EP | 252607 A2 | 9/1992 |
| WO | 9922649 A2 | 5/1999 |

(Continued)

OTHER PUBLICATIONS

The gastroesophageal flap valve: in vitro and in vivo observations; Lucius D. Hill et al.; Gastrointestinal Endoscopy; vol. 44, No. 5, 1996; pp. 541-547; abstract.

(Continued)

*Primary Examiner* — Gregory Anderson
*Assistant Examiner* — Christina Lauer
(74) *Attorney, Agent, or Firm* — Fulwider Patton LLP

(57) ABSTRACT

A device for reducing the volume of a hollow body organ includes a tissue port and a plurality of fasteners. The fasteners may be coupled to a flexible filament, such as a suture, which is tensioned to constrict the hollow body organ to achieve volume reduction.

3 Claims, 10 Drawing Sheets

(56) References Cited

U.S. PATENT DOCUMENTS

| | | | |
|---|---|---|---|
| 5,041,129 A | 8/1991 | Hayhurst et al. |
| 5,080,543 A | 1/1992 | Murphy |
| 5,088,979 A | 2/1992 | Filipi et al. |
| 5,254,126 A | 10/1993 | Filipi et al. |
| 5,314,473 A | 5/1994 | Godin |
| 5,403,326 A | 4/1995 | Harrison et al. |
| 5,411,508 A | 5/1995 | Bessler et al. |
| 5,411,520 A | 5/1995 | Nash et al. |
| 5,549,621 A | 8/1996 | Bessler et al. |
| 5,571,074 A | 11/1996 | Buckman et al. |
| 5,571,116 A | 11/1996 | Bolanos et al. |
| 5,626,614 A | 5/1997 | Hart |
| 5,676,674 A | 10/1997 | Bolanos et al. |
| 5,713,903 A | 2/1998 | Sander et al. |
| 5,759,151 A | 6/1998 | Sturges |
| 5,810,882 A | 9/1998 | Bolduc et al. |
| 5,814,054 A | 9/1998 | Kortenbach et al. |
| 5,861,036 A | 1/1999 | Godin |
| 5,879,372 A | 3/1999 | Bartlett et al. |
| 5,887,594 A | 3/1999 | LoCicero |
| 5,897,562 A | 4/1999 | Bolanos et al. |
| 5,938,668 A | 8/1999 | Scirica et al. |
| 6,086,600 A | 7/2000 | Kortenbach |
| 6,098,629 A | 8/2000 | Johnson et al. |
| 6,113,609 A | 9/2000 | Adams |
| 6,113,611 A | 9/2000 | Allen et al. |
| 6,142,957 A | 11/2000 | Diamond et al. |
| 6,174,323 B1 * | 1/2001 | Biggs et al. ............... 606/232 |
| 6,254,642 B1 | 7/2001 | Taylor |
| 6,264,700 B1 | 7/2001 | Kilcoyne et al. |
| 6,302,311 B1 | 10/2001 | Adams et al. |
| 6,302,917 B1 | 10/2001 | Dua et al. |
| 6,312,437 B1 | 11/2001 | Kortenbach |
| 6,315,789 B1 | 11/2001 | Cragg |
| 6,419,669 B1 | 7/2002 | Frazier et al. |
| 6,428,548 B1 | 8/2002 | Durgin et al. |
| 6,447,524 B1 | 9/2002 | Knodel et al. |
| 6,743,239 B1 | 6/2004 | Kuehn et al. |
| 6,773,440 B2 * | 8/2004 | Gannoe et al. ............... 606/142 |
| 6,773,441 B1 | 8/2004 | Laufer et al. |
| 6,790,214 B2 | 9/2004 | Kraemer et al. |
| 6,835,200 B2 | 12/2004 | Laufer et al. |
| 6,916,332 B2 | 7/2005 | Adams |
| 6,921,361 B2 | 7/2005 | Suzuki et al. |
| 7,022,118 B2 | 4/2006 | Ariura et al. |
| 7,037,344 B2 | 5/2006 | Kagan et al. |
| 7,074,229 B2 | 7/2006 | Adams et al. |
| 7,083,630 B2 | 8/2006 | DeVries et al. |
| 7,220,266 B2 | 5/2007 | Gambale |
| 7,347,863 B2 | 3/2008 | Rothe et al. |
| 7,618,426 B2 | 11/2009 | Ewers et al. |
| 7,632,287 B2 | 12/2009 | Baker et al. |
| 7,678,123 B2 | 3/2010 | Chanduszko |
| 7,713,277 B2 | 5/2010 | Laufer et al. |
| 7,776,057 B2 | 8/2010 | Laufer et al. |
| 7,850,704 B2 | 12/2010 | Burnett et al. |
| 7,857,184 B2 | 12/2010 | Viola |
| 7,857,823 B2 | 12/2010 | Laufer et al. |
| 7,866,526 B2 | 1/2011 | Green et al. |
| 7,942,887 B2 | 5/2011 | Kraemer et al. |
| 7,951,157 B2 | 5/2011 | Gambale |
| 7,954,687 B2 | 6/2011 | Zemlok et al. |
| 7,955,340 B2 | 6/2011 | Michlitsch et al. |
| 8,057,494 B2 | 11/2011 | Laufer et al. |
| 8,252,009 B2 | 8/2012 | Weller et al. |
| 8,277,468 B2 | 10/2012 | Laufer et al. |
| 8,308,765 B2 | 11/2012 | Saadat et al. |
| 8,343,175 B2 | 1/2013 | Ewers et al. |
| 8,574,243 B2 | 11/2013 | Saadat et al. |
| 2002/0022853 A1 | 2/2002 | Swanson et al. |
| 2002/0035370 A1 | 3/2002 | Kortenbach |
| 2002/0040226 A1 | 4/2002 | Laufer et al. |
| 2002/0055772 A1 | 5/2002 | McGuckin, Jr. et al. |
| 2002/0072761 A1 | 6/2002 | Abrams et al. |
| 2002/0078967 A1 | 6/2002 | Sixto, Jr. et al. |
| 2002/0082621 A1 | 6/2002 | Schurr et al. |
| 2002/0143349 A1 | 10/2002 | Gifford, III et al. |
| 2002/0183765 A1 | 12/2002 | Adams |
| 2002/0198541 A1 | 12/2002 | Smith et al. |
| 2003/0023230 A1 | 1/2003 | Lewis et al. |
| 2003/0055442 A1 | 3/2003 | Laufer et al. |
| 2003/0065359 A1 | 4/2003 | Weller et al. |
| 2003/0093117 A1 | 5/2003 | Saadat |
| 2003/0120289 A1 | 6/2003 | McGuckin, Jr. et al. |
| 2003/0120292 A1 | 6/2003 | Park et al. |
| 2003/0171760 A1 | 9/2003 | Gambale |
| 2003/0187465 A1 | 10/2003 | Bailly et al. |
| 2003/0191497 A1 | 10/2003 | Cope |
| 2003/0216613 A1 | 11/2003 | Suzuki et al. |
| 2003/0216754 A1 | 11/2003 | Kraemer et al. |
| 2003/0220657 A1 | 11/2003 | Adams |
| 2004/0044304 A1 | 3/2004 | Hill et al. |
| 2004/0044364 A1 | 3/2004 | DeVries et al. |
| 2004/0087976 A1 | 5/2004 | DeVries et al. |
| 2004/0093024 A1 | 5/2004 | Lousararian et al. |
| 2004/0116949 A1 | 6/2004 | Ewers et al. |
| 2004/0133236 A1 | 7/2004 | Chanduszko |
| 2004/0138529 A1 | 7/2004 | Wiltshire et al. |
| 2004/0147958 A1 | 7/2004 | Lam et al. |
| 2004/0148034 A1 | 7/2004 | Kagan et al. |
| 2004/0153102 A1 | 8/2004 | Therin et al. |
| 2004/0153103 A1 | 8/2004 | Schwartz et al. |
| 2004/0162568 A1 | 8/2004 | Saadat et al. |
| 2004/0215216 A1 | 10/2004 | Gannoe et al. |
| 2004/0236357 A1 | 11/2004 | Kraemer et al. |
| 2004/0243223 A1 | 12/2004 | Kraemer et al. |
| 2005/0004575 A1 | 1/2005 | Sgro et al. |
| 2005/0017781 A1 | 1/2005 | Honda |
| 2005/0043759 A1 | 2/2005 | Chanduszko |
| 2005/0075653 A1 | 4/2005 | Saadat et al. |
| 2005/0085829 A1 | 4/2005 | Kraemer et al. |
| 2005/0154405 A1 | 7/2005 | Kraemer et al. |
| 2005/0177176 A1 | 8/2005 | Gerbi et al. |
| 2005/0187565 A1 | 8/2005 | Baker et al. |
| 2005/0192599 A1 * | 9/2005 | Demarais ............... 606/151 |
| 2005/0203547 A1 | 9/2005 | Weller et al. |
| 2005/0216040 A1 | 9/2005 | Gertner et al. |
| 2005/0228413 A1 | 10/2005 | Binmoeller et al. |
| 2005/0247320 A1 | 11/2005 | Stack et al. |
| 2005/0251176 A1 | 11/2005 | Swanstrom et al. |
| 2006/0009789 A1 | 1/2006 | Gambale et al. |
| 2006/0151568 A1 * | 7/2006 | Weller et al. ............... 227/175.1 |
| 2006/0190018 A1 | 8/2006 | Baker et al. |
| 2006/0253130 A1 | 11/2006 | Wolniewicz |
| 2006/0253142 A1 | 11/2006 | Bjerken |
| 2007/0021756 A1 | 1/2007 | Kortenbach |
| 2007/0021760 A1 | 1/2007 | Kelleher |
| 2007/0112363 A1 | 5/2007 | Adams |
| 2007/0129738 A1 | 6/2007 | Kraemer et al. |
| 2007/0191870 A1 | 8/2007 | Baker et al. |
| 2007/0191871 A1 | 8/2007 | Baker et al. |
| 2007/0219566 A1 | 9/2007 | Gambale |
| 2007/0225736 A1 * | 9/2007 | Zeiner et al. ............... 606/148 |
| 2007/0276409 A1 * | 11/2007 | Ortiz et al. ............... 606/139 |
| 2008/0015618 A1 | 1/2008 | Sonnenschein et al. |
| 2008/0287966 A1 | 11/2008 | Kraemer et al. |
| 2008/0294179 A1 | 11/2008 | Balbierz et al. |
| 2009/0177214 A1 | 7/2009 | Adams |
| 2009/0198254 A1 | 8/2009 | Laufer et al. |
| 2009/0236388 A1 | 9/2009 | Cole et al. |
| 2010/0241139 A1 | 9/2010 | Harshman |
| 2011/0196391 A1 | 8/2011 | Forsell |
| 2011/0213390 A1 | 9/2011 | Kraemer et al. |

FOREIGN PATENT DOCUMENTS

| | | |
|---|---|---|
| WO | 9960931 A1 | 12/1999 |
| WO | 0053102 A1 | 9/2000 |
| WO | 0078227 A1 | 12/2000 |
| WO | 0132084 A1 | 5/2001 |
| WO | 0135834 A1 | 5/2001 |
| WO | 0164964 A1 | 9/2001 |
| WO | 0167964 A2 | 9/2001 |
| WO | 0185034 A1 | 11/2001 |

(56) References Cited

FOREIGN PATENT DOCUMENTS

| WO | 0189391 | A1 | 11/2001 |
|---|---|---|---|
| WO | 0224058 | A2 | 3/2002 |
| WO | 0224080 | A2 | 3/2002 |
| WO | 0228289 | A1 | 4/2002 |
| WO | 02082621 | A1 | 10/2002 |
| WO | 02096327 | A2 | 12/2002 |
| WO | 03061480 | A1 | 7/2003 |
| WO | 03099140 | A1 | 12/2003 |
| WO | 2004019787 | A2 | 3/2004 |
| WO | 2004019788 | A2 | 3/2004 |
| WO | 2004049982 | A2 | 6/2004 |
| WO | 2004069055 | A2 | 8/2004 |
| WO | 2005065412 | A2 | 7/2005 |
| WO | 2005081817 | A2 | 9/2005 |
| WO | 2006023764 | A2 | 3/2006 |
| WO | 2006034484 | A2 | 3/2006 |
| WO | 2006081368 | A2 | 8/2006 |
| WO | 2007002817 | A2 | 1/2007 |
| WO | 2007064713 | A2 | 6/2007 |
| WO | 2010087756 | A1 | 8/2010 |

OTHER PUBLICATIONS

Reappraisal of the flap valve mechanism in the gastroesophageal junction: A study of a new valvuloplasty procedure in cadavers; KjellB.A. Thor et al.; Acta Chir Scand 153:25-28, 1987; abstract.
The Plicator Procedure; 1 page; abstract.
Chuttani, MD. et al., "A novel endoscopic full-thickness plicator for treatment of GERD: an animal model study". Gastrointestinal Endoscopy, vol. 56, No. 1, 2002, pp. 116-122; abstract.
Jobe, et al., "Endoscopic Appraisal of the Gastroesophageal Valve After Antireflux Surgery", American Journal of Gastroenterology, ISSN 0002-9270; abstract.
International Search Report for PCT/US2012/054328.

* cited by examiner

CONNECTED FASTENERS, DELIVERY DEVICE AND METHOD

This application claims priority to Provisional Application No. 60/879,402, filed Jan. 8, 2007.

BACKGROUND OF THE INVENTION

The present invention is directed to methods and devices for applying fasteners to the stomach or esophagus. The present invention is also directed to methods and devices for restricting the esophagus and/or stomach.

SUMMARY

The delivery device carries fasteners connected to suture. A suture holder such as a sliding knot or adjustable clamp or a crimp sleeve can adjust the length of the connected suture smaller or larger. In the preferred embodiment the suture holder is pre-attached to the suture. For example the suture holder can connect the ends of the suture to form a loop. The delivery device is introduced through the mouth and esophagus into the stomach. The delivery device fastens the tissue with the fasteners.

An adjusting device pulls the suture, which in turn pull the fasteners and the fastened stomach tissue. This reduces the internal size of the stomach and creates a restrictive gastric pouch.

The delivery device has a tissue chamber and one or more tissue ports. The tissue chamber can be radially collapsed for introduction into and removal from the patient. After entering the stomach, the tissue chamber can be radially expanded. This reduces folding of the stomach during tissue retraction and enables more accurate placement of fasteners. Tissue is retracted through the tissue port into the tissue chamber and then fastened. For example the tissue can be retracted by suction or mechanical grasping.

The suture and fasteners can be pre-loaded on and in the delivery device such that after fastening the fasteners and suture are completely releasable from the delivery device without the need to separate the parts of the device.

The suture can wrap around the outside of the tissue chamber as it passes from one tissue port to the next. The suture can be partially or completely covered for easier introduction of the device into the patient. For example the suture loop can be placed in a recessed groove. The suture can be at least partially covered by a membrane with a releasable adhesive bond to the device, a tearable membrane, a flap with a free edge, or by a removable sheath.

The fasteners and suture can be delivered in a position and sequence such that the suture forms one of several desired shapes such as an approximately circular loop or a zigzag or a figure eight or overlapping diametral segments. These shapes affect the shape of the tissue.

DESCRIPTION OF THE PREFERRED EMBODIMENTS

Figure 1:
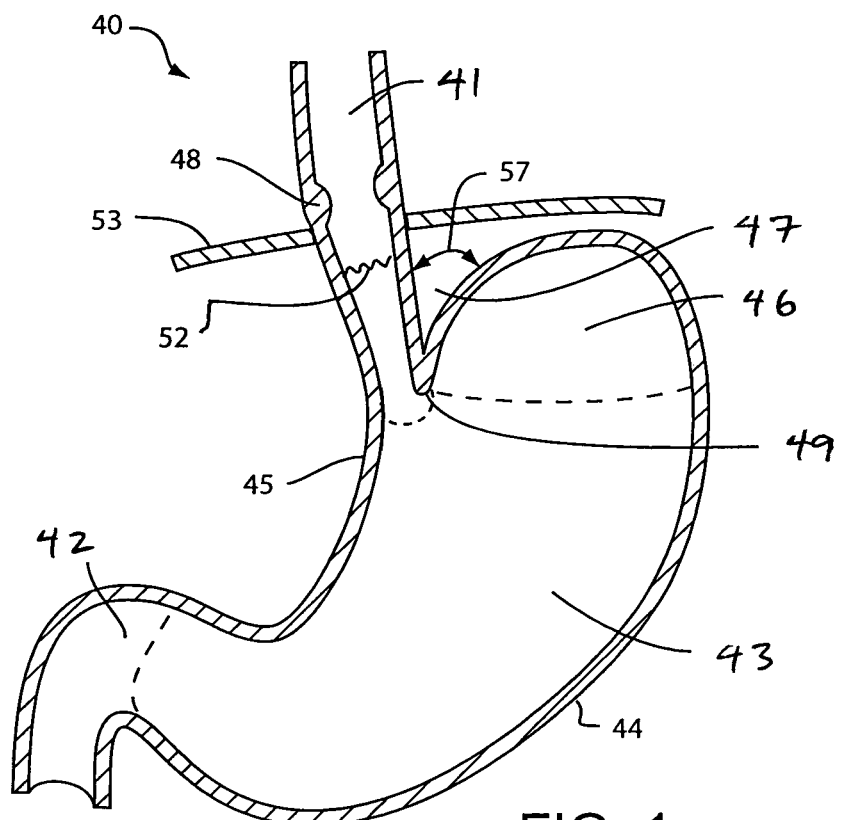
FIG. 1 shows a stomach.

Referring to FIG. 1, a gastroesophageal region 40 is shown which includes an esophagus 41 leading to a stomach 43. The stomach 43 includes a greater curvature 44 and a lesser curvature 45 and a fundus 46. A cardiac notch 47 is formed at the junction between the esophagus 41 and the stomach 43 which forms an angle of HIS 57. A gastroesophageal junction 52 lies between a lower esophageal sphincter 48 and a gastroesophageal flap valve 49. A diaphragm 53 extends around the stomach 43.

Figure 2:
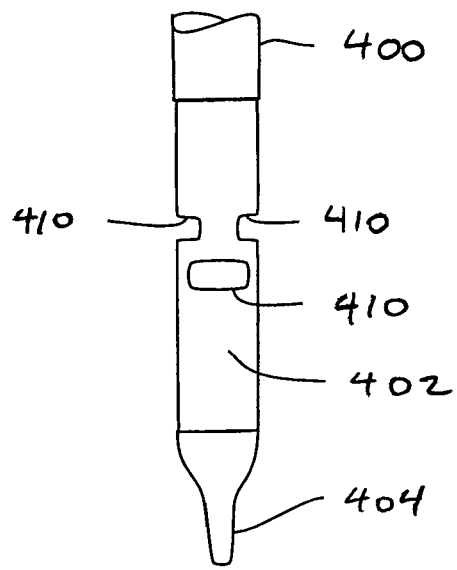
FIG. 2 shows a fastener delivery device having a tissue chamber and tissue ports.
Figure 3:
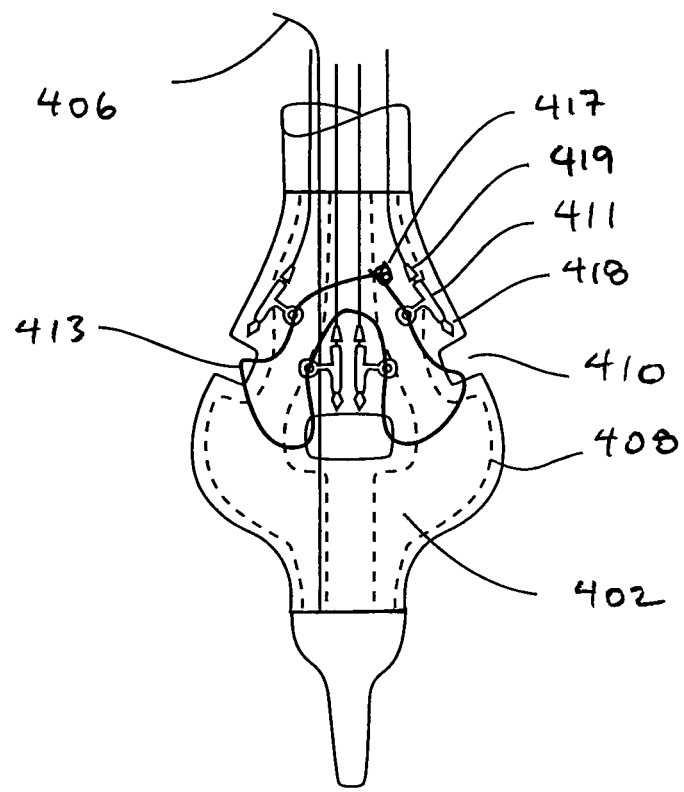
FIG. 3 shows a radially expandable tissue chamber.
Figure 4:
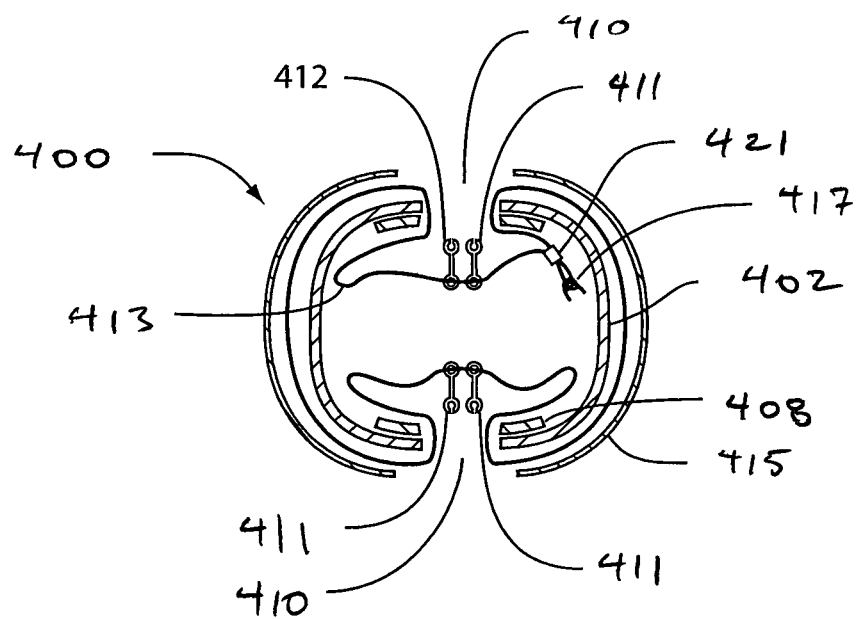
FIG. 4 shows a cross section of the delivery device with fasteners connected by a suture loop.

Referring to FIGS. 2-4, a delivery device 400 is shown which has a tissue chamber 402 and one or more tissue ports 410. Tissue is drawn into the tissue ports 410 and fastened together with fasteners 411. Tissue is drawn into the tissue ports 410 using suction although a mechanical grasper may also be used. The device 400 may include a valve 404, such as a duck bill valve, at the distal end which may receive an endoscope as is known in the art.

Referring to FIG. 3 and FIG. 4, the tissue chamber 402 may be expanded by tensioning a control line 406 which causes the tissue chamber 402 to expand and bow outward. Expansion of the tissue chamber 402 may help to prevent excessive folding of the tissue while permitting a relatively large amount of tissue to create the tissue fold. The device 400 includes struts 408 which support the tissue chamber 402 and help to form a desired shape when the tissue chamber 402 is expanded.

The device 400 is loaded with a number of fasteners 411 and a flexible filament 413 such as suture 415 or the like. The filament 413 may form a closed loop with a knot 417 or other suitable method of securing one part of the filament 413 to another to maintain tension on the filament 413 as described below. The filament 413 may extend out of one of the tissue ports 410 and re-enter the device through another tissue port 410 as shown in FIG. 3. The filament 413 may be covered by a flap 415 which covers the filament 413 while permitting release of the filament 413 through a free edge.

Figure 5:
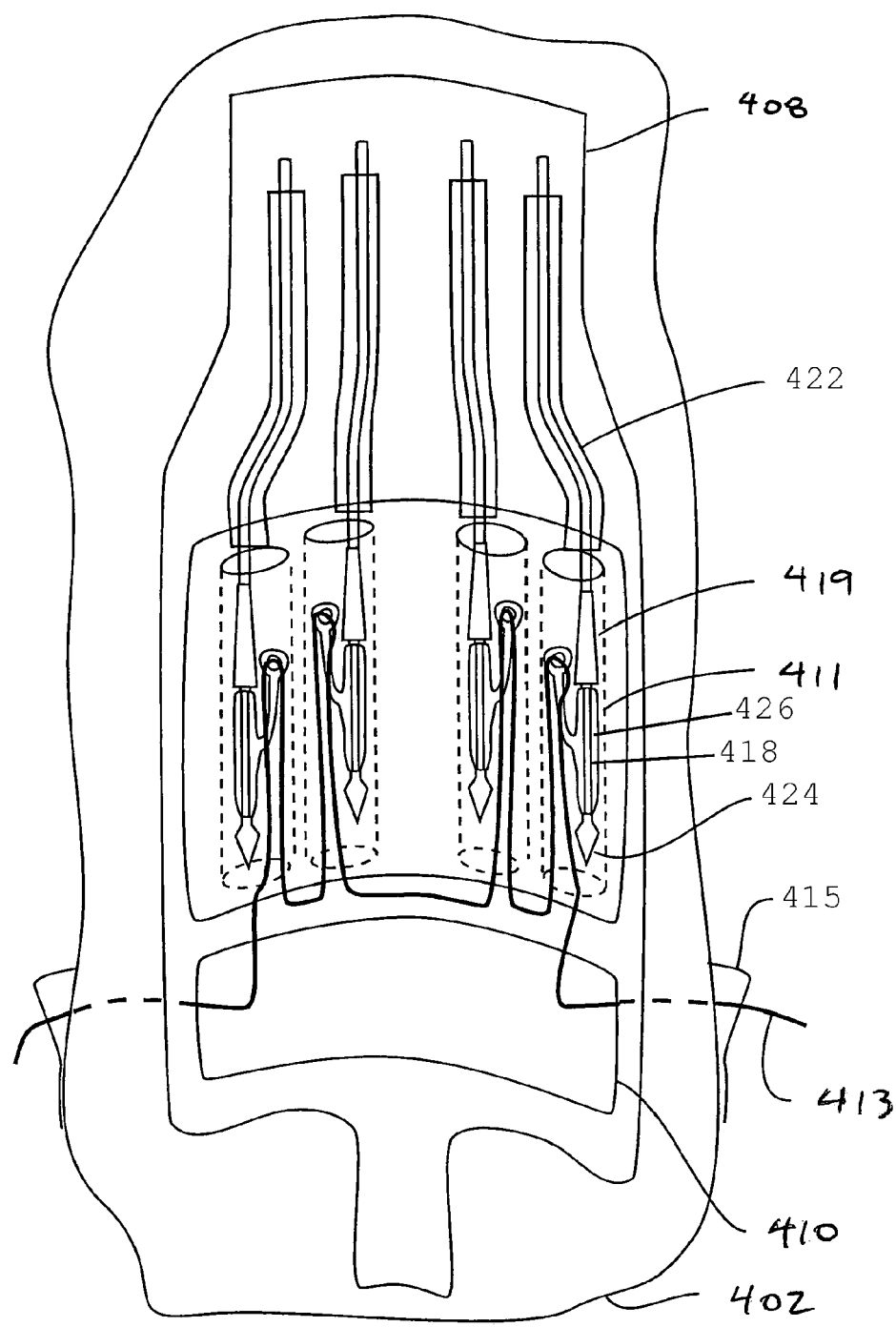
FIG. 5 shows a cutaway portion of the device viewed from inside the tissue chamber.

Referring to FIG. 5, the fasteners and filament 413 are shown positioned above the tissue port. The fasteners 411 are mounted to a stylet 418 having a pusher 419 that is positioned in a stylet tube 422. The stylet 418 has a sharp tip 424 which is used to penetrate tissue. The fastener 411 may have a groove 426 or other feature which permits release of the fastener 411 from the stylet 418. A number of fasteners 411 may be deployed through each of the tissue ports 410 as explained below. The flap 415 covers the portion of the filament 413 extending from one of the tissue ports to an adjacent tissue port 410.

Figure 6:
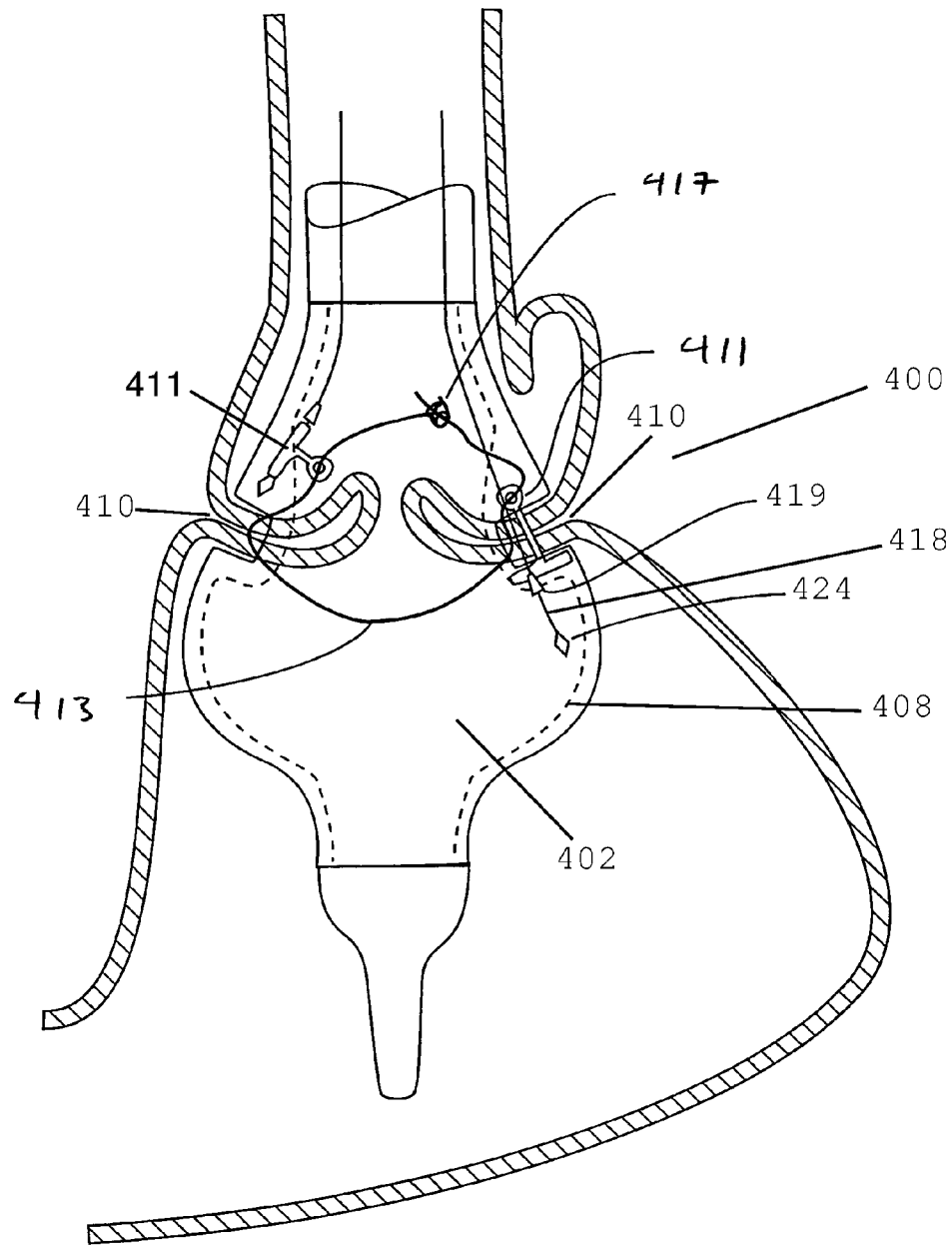
FIG. 6 shows the fastener delivery device in the stomach. The tissue chamber is radially expanded. Tissue is retracted into the tissue chamber through the tissue ports.
Figure 7:
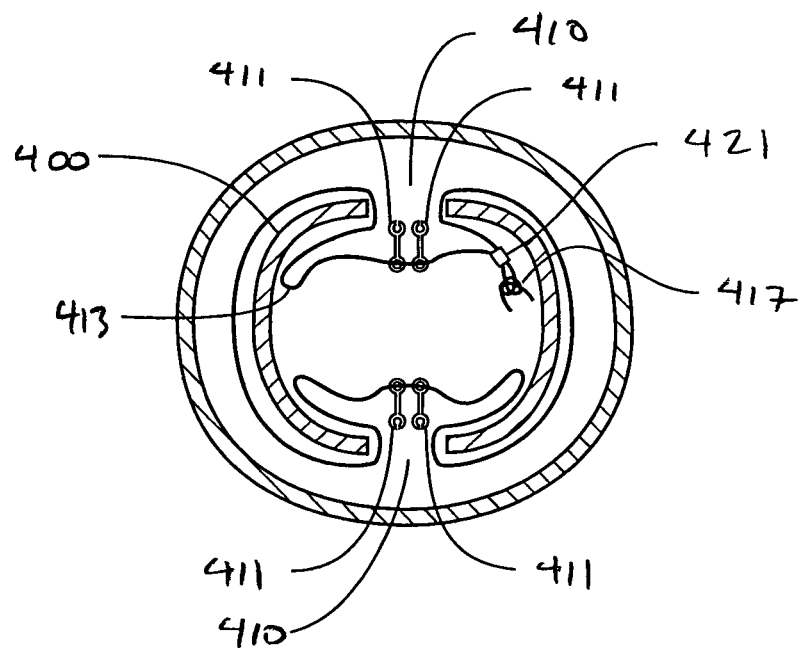
FIG. 7 shows a cross sectional view of the fastener delivery device in the stomach.
Figure 8:
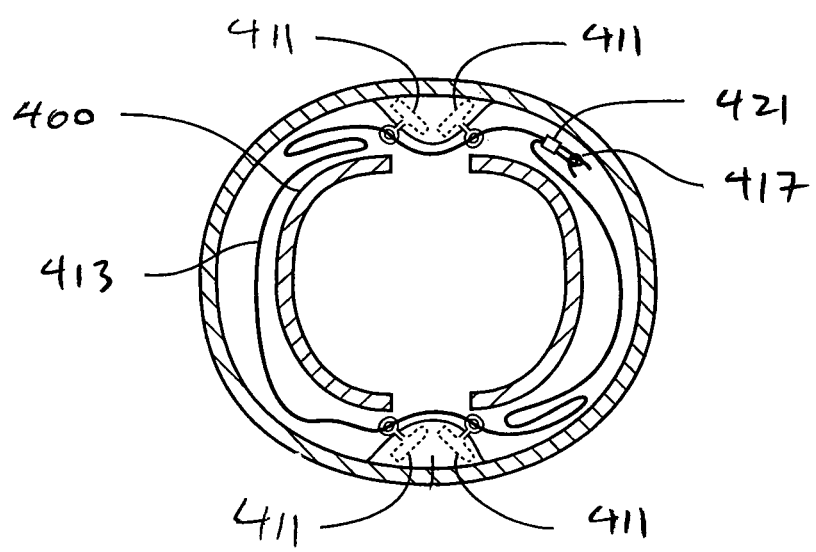
FIG. 8 shows fasteners deployed in a sequence to place a suture loop in an approximately circumferential orientation.
Figure 9:
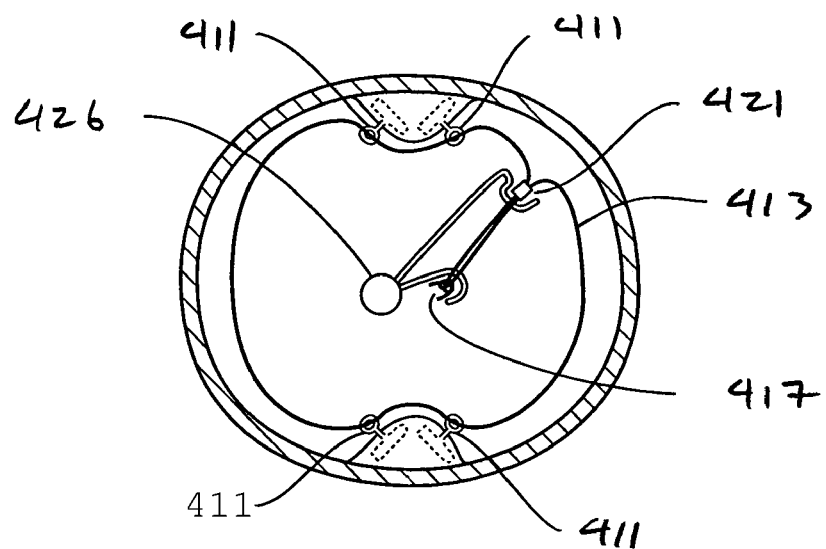
FIG. 9 shows the adjusting device sliding the suture holder to reduce the length of the suture loop.
Figure 10:
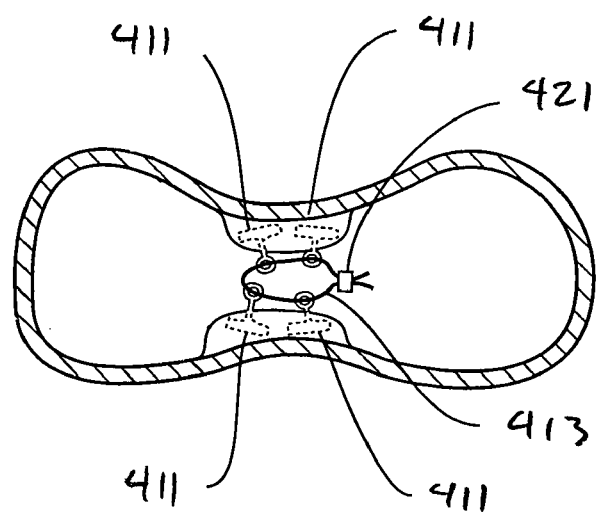
FIG. 10 shows the suture tightened to reduce the luminal area of the stomach.

Referring now to FIG. 6, the device 400 is shown with the tissue chamber 402 expanded. Tissue is drawn into the tissue ports 410 to form a tissue fold in each of the tissue ports 410. The fasteners 411 are then driven through the tissue folds using the stylet 418. The filament 413 may then be tensioned to draw the fasteners 411 together. In this manner, a hollow body structure such as the stomach may be reduced in volume. FIGS. 7 and 8 show two fasteners 411 deployed from each tissue port 410. Referring to FIG. 9, the filament 413 may be tensioned to draw the tissue structures together as shown in FIG. 10 to form two lobes in the stomach. Tension on the filament 413 may be applied and maintained using a tightening device 426 which may create a knot or use a sleeve 421 to tighten and maintain tension on the filament 413.

Figure 11:
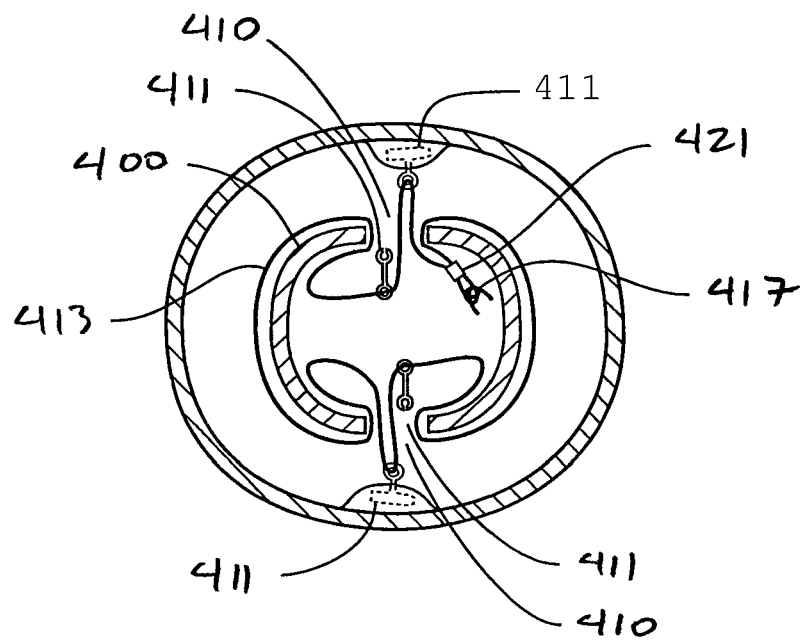
FIG. 11 shows two fasteners deployed from two tissue ports approximately 180 degrees apart.
Figure 12:
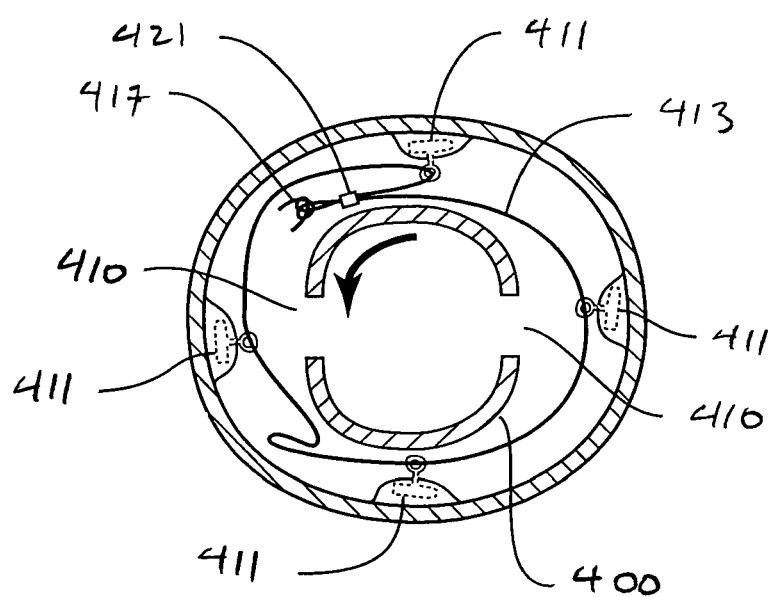
FIG. 12 shows rotating the device approximately 90 degrees and deploying two more fasteners approximately midway between the first two fasteners.
Figure 13:
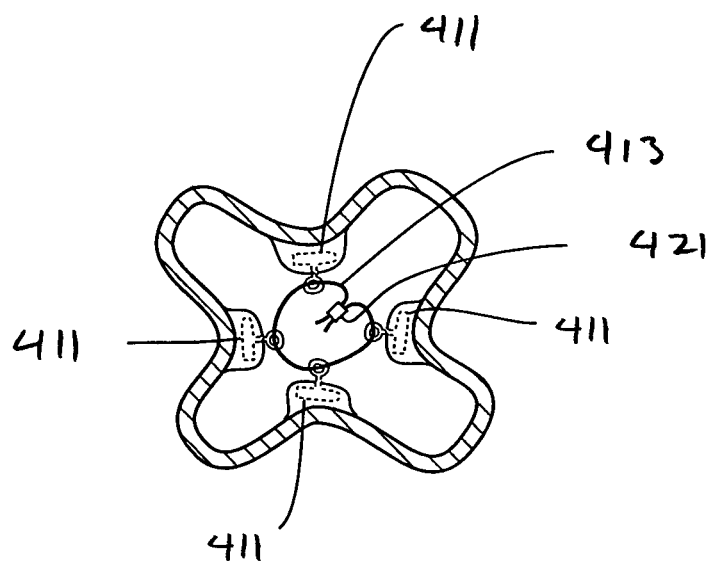
FIG. 13 shows the suture tightened to reduce the luminal area of the stomach.
Figure 14:
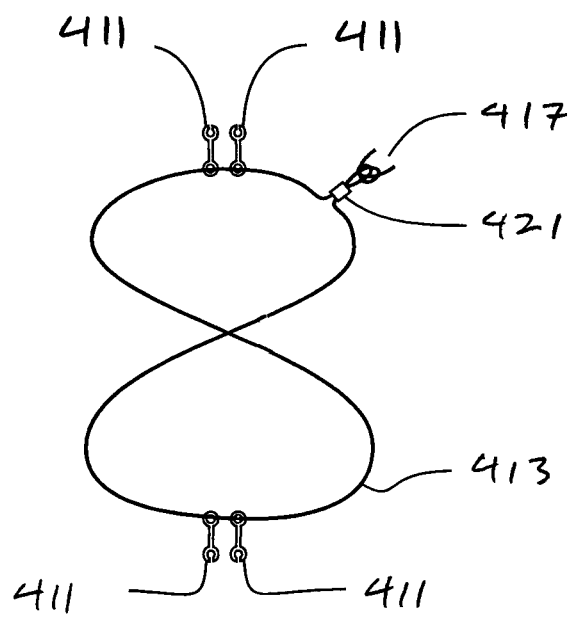
FIG. 14 shows the suture before loading into the device in which the suture loop crosses itself to form a "figure 8" shape.
Figure 15:
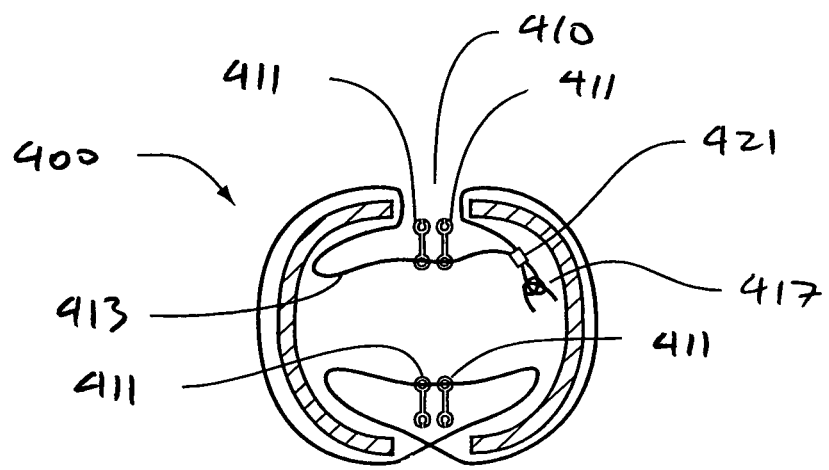
FIG. 15 shows the crossed suture and fasteners loaded into the delivery device.
Figure 16:
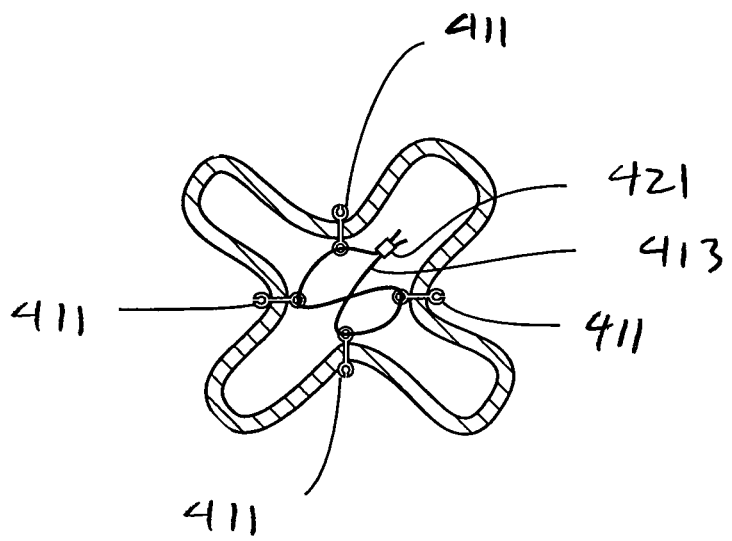
FIG. 16 shows the "figure 8" loop in the stomach, with the suture oriented partly circumferential and partly diametral. In this example each fastener penetrates a single layer of tissue.

Referring now to FIGS. 11-13, still another method of using the device 400 is shown. One fastener 411 is delivered through each of the tissue ports 410 as shown in FIG. 11. The device 400 is then rotated to the position of FIG. 12 and two more fasteners 411 are deployed. The filament 413 may then be tensioned to form four lobes in the stomach. Referring to FIGS. 14-16, the filament 413 may also be configured to extend across the hollow body structure in a pattern similar to a figure-8. FIG. 15 shows the filament 413 loaded onto the delivery device 400. Two of the fasteners 411 are deployed through the tissue ports 410 and the device 400 is rotated and two more fasteners 411 are deployed. The filament 413 is then tensioned to draw the tissue structure together as shown in FIG. 16.

Figure 17:
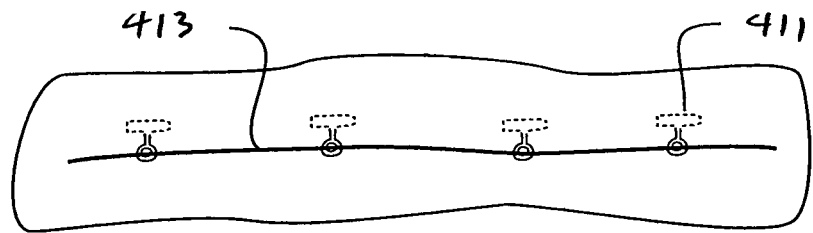
FIG. 17 shows an intraluminal view of fasteners deployed into tissue.
Figure 18:
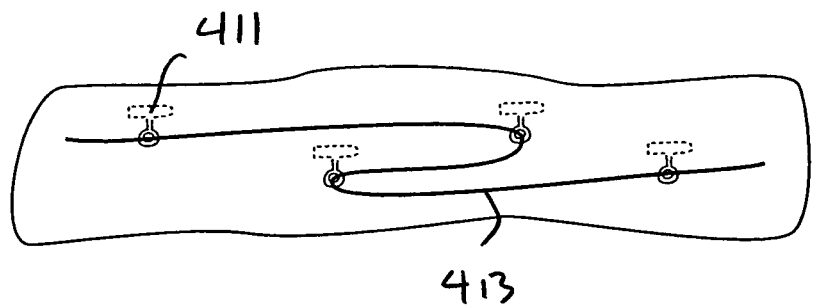
FIG. 18 shows fasteners deployed to place the suture in a "backstitched" orientation.
Figure 19:
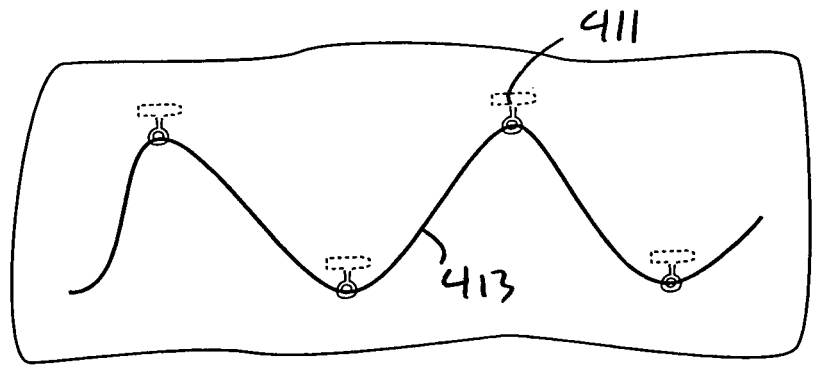
FIG. 19 shows fasteners deployed at varying axial heights to place the suture in a zigzag orientation.

FIGS. 17-19 show various configurations for the filament 413. FIG. 17 shows the filament 413 deployed in an approximately planar ring. FIG. 18 shows the filament 413 in a backstitched orientation. FIG. 18 shows fasteners can be deployed to place the suture in a "backstitched" orientation. For example, the device can be rotated between sequential fastener deployments. As may be appreciated from the figure, when the suture is tightened further the fasteners will pull tissue sideways.

FIG. 19 shows the filament 413 in a zigzag orientation at varying axial heights. A zigzag loop can increase the number of tissue folds such that the outlet area from a gastric pouch is reduced more than from a non zigzag loop. As may be appreciated from FIG. 19, when the suture is tightened further the zigzag will decrease in axial amplitude and the fasteners will pull tissue axially closer together as well as circumferentially closer together.

Placing the fasteners in the desired pattern alters the shape of the suture loop. In turn this alters the suture's direction of pull on the fasteners and the fasteners direction of pull on the tissue. This can be used to cause the tissue to fold in beneficial ways.

Fastening a single suture such that multiple segments have tension components in the same direction increases the force on the tissue in that direction. For example a diametrically oriented suture can be more efficient at pulling tissue radially inward than a circumferential suture.

The tensioning element or suture holder may be a sliding knot such as a Roeder knot. The tensioning element or not may also be a clip that is crimped to the suture loop or a sleeve that can slide on the suture loop. The adjusting device can also be a flexible endoluminal crimper that crimps the suture holder to hold the suture.

The present invention has been described with reference to preferred embodiments; however, numerous changes may be made without departing from the scope of the invention.

The invention claimed is:

1. A method for reducing the volume of a hollow body structure, comprising the steps of:
providing a device having a body and a tissue chamber coupled to the body, the tissue chamber being expandable, the device also having a plurality of tissue ports configured to draw a fold of tissue into each of the tissue ports using suction, the tissue ports being positioned along the tissue chamber so that the fold of tissue extends into the tissue chamber, the device also having a plurality of fasteners and a flexible filament carried by the body, the fasteners configured to be delivered through the fold of tissue extending into the tissue port and held in the tissue port using suction, the flexible filament being coupled to each of the plurality of fasteners and extending through one of the tissue ports and entering another of the tissue ports prior to deployment;
positioning the device in a hollow body structure;
expanding the tissue chamber into a desired shaped using a plurality of flexible struts;
drawing a fold of tissue into one of the tissue ports using suction;
advancing a sharp tip of a stylet through the fold of tissue;
advancing at least one of the fasteners over the stylet and into the fold of tissue by advancing a pusher on the stylet to push the fastener into the fold of tissue;
moving the tissue port;
drawing a second fold of tissue into another one of the tissue ports using suction after the moving step, the second fold of tissue being spaced apart from the first fold of tissue;
advancing at least one of the fasteners over the stylet and into the second fold of tissue, the flexible filament extending through the fasteners in the first and second folds of tissue;
tensioning the flexible filament using a tensioning device implanted inside the body to pull on the fasteners thereby moving the first and second folds of tissue towards one another and securing the flexible filament with a knot inside the body.

2. The method of claim 1, wherein:
the providing step is carried out with the device having the plurality of fasteners configured to be delivered at each of the plurality of tissue ports.

3. The method of claim 1, wherein:
the providing step is carried out with the device having a tensioning element coupled to the flexible filament, the tensioning element being configured to apply tension to the flexible filament.

* * * * *